United States Patent [19]
Dumas et al.

[11] Patent Number: 5,720,721
[45] Date of Patent: Feb. 24, 1998

[54] METHOD FOR MONITORING VISCOSITY AND OCCLUSIONS IN AN ENTERAL FEEDING PUMP DELIVERY

[75] Inventors: Chris Dumas, Escondido, Calif.; Sean Winterer, Sandy, Utah

[73] Assignee: Zevex, Inc., Murray, Utah

[21] Appl. No.: 642,526

[22] Filed: May 3, 1996

Related U.S. Application Data

[63] Continuation-in-part of Ser. No. 435,714, May 5, 1995, Pat. No. 5,514,102.

[51] Int. Cl.$^6$ ................................................ A61M 31/00
[52] U.S. Cl. ........................... 604/67; 604/49; 604/65; 604/118
[58] Field of Search ........................... 604/49, 65, 30, 604/31, 34, 66, 67, 118, 119, 246

[56] References Cited

U.S. PATENT DOCUMENTS

| | | |
|---|---|---|
| D. 284,221 | 6/1986 | Kerkut . |
| 4,460,355 | 7/1984 | Layman . |
| 4,515,588 | 5/1985 | Amendolia . |
| 4,559,034 | 12/1985 | Kiita et al. . |
| 4,613,325 | 9/1986 | Abrams . |
| 4,784,576 | 11/1988 | Bloom et al. . |
| 4,784,577 | 11/1988 | Ritson et al. . |
| 4,838,865 | 6/1989 | Flank et al. . |
| 4,863,425 | 9/1989 | Slate et al. . |
| 4,950,244 | 8/1990 | Fellingham et al. . |
| 4,976,687 | 12/1990 | Martin . |
| 4,994,035 | 2/1991 | Mokros . |
| 5,037,386 | 8/1991 | Marcus et al. . |
| 5,096,385 | 3/1992 | Georgi et al. . |
| 5,098,384 | 3/1992 | Abrams . |
| 5,098,387 | 3/1992 | Wiest et al. . |
| 5,137,522 | 8/1992 | Bron . |
| 5,195,960 | 3/1993 | Hossain et al. . |
| 5,312,334 | 5/1994 | Hara et al. . |
| 5,336,181 | 8/1994 | Nakao et al. . |
| 5,346,477 | 9/1994 | Edwards et al. . |

*Primary Examiner*—Michael Powell Buiz
*Assistant Examiner*—N. Kent Gring
*Attorney, Agent, or Firm*—Thorpe, North & Western, LLP

[57] ABSTRACT

A pressure monitoring enteral feeding system and method are disclosed including a housing having a pair of channels for receiving a pump tubing segment which connects an intake line and an output line of a delivery set, and for holding the pump tubing segment adjacent a motor unit. A pair of pressure sensors are disposed along the channels to monitor the pressure in the pump tubing segment so as to warn a user when an undesirable pressure has developed either upstream or downstream from the motor unit, and to adjust rate based on the upstream pressure. The housing may also include a lockable cover to securely hold the pump tubing segment in the channels and in firm contact with the pressure sensors. In accordance with one aspect of the invention, the pressure sensors are used to determine the actual output of the enteral feeding pump by monitoring strain in the delivery set. The pump can then make adjustments to the length of time the rotor turns during each cycle to ensure that partial occlusions, viscosity changes and back pressure do not interfere with proper dosing.

29 Claims, 8 Drawing Sheets

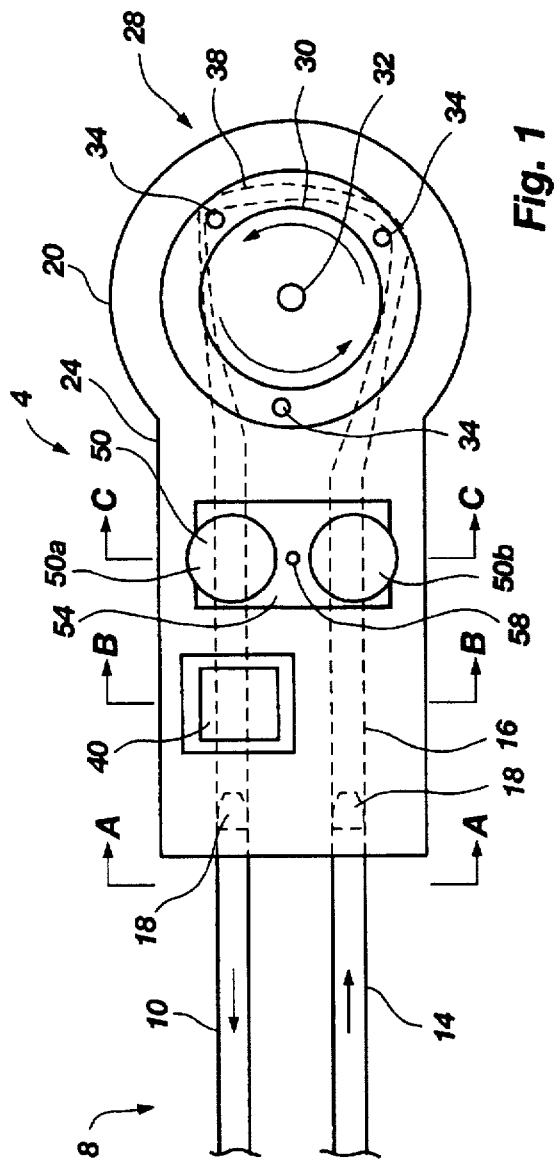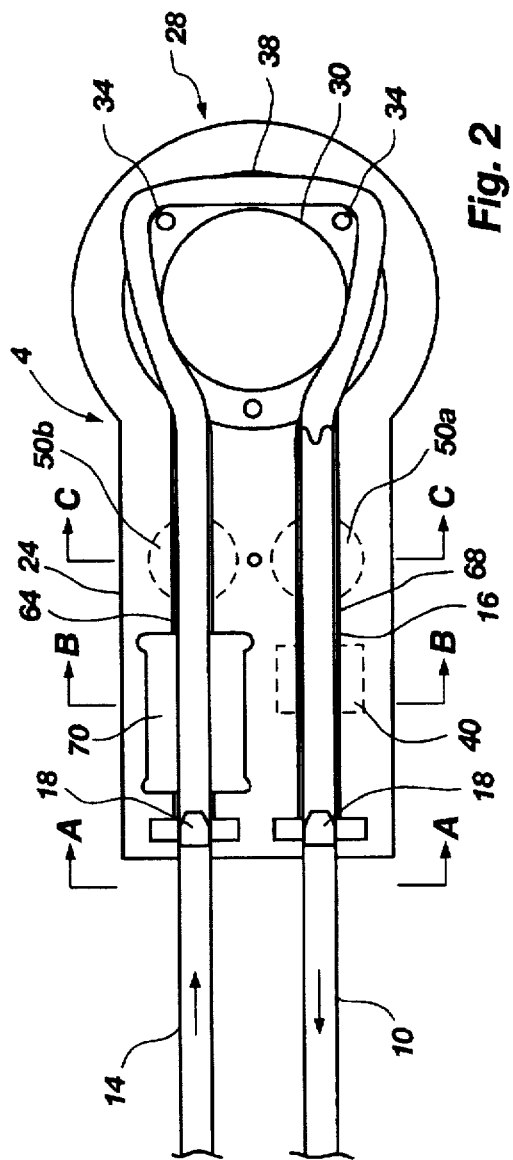

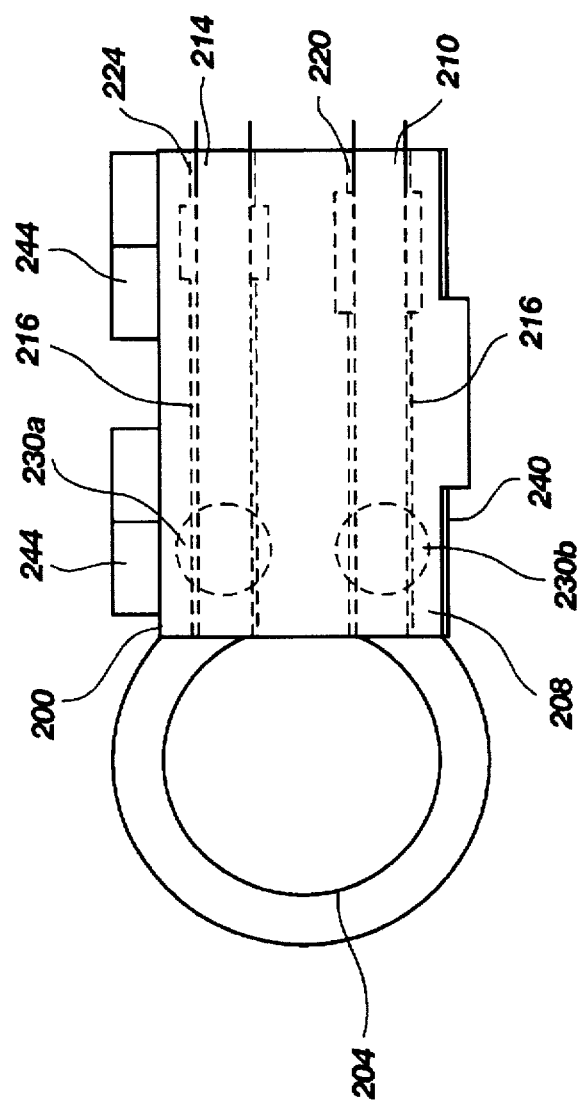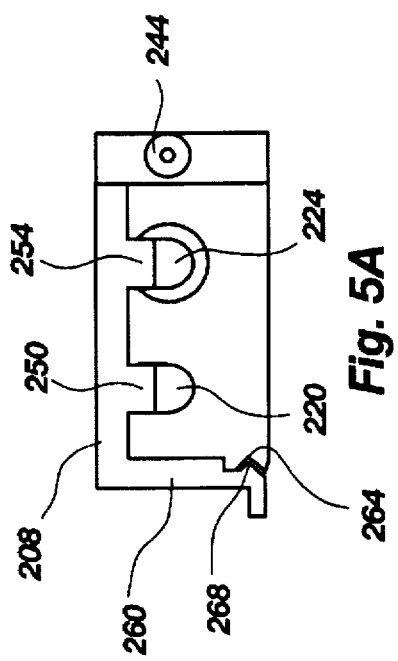

```
┌─────────────────────────────────────────────────────────────┐
│  Determine pressure within upstream portion of the pump tubing segment │
│      while motor unit is not rotating to obtain a stopped strain.      │
└─────────────────────────────────────────────────────────────┘
                              │
                              ▼
┌─────────────────────────────────────────────────────────────┐
│   Determine pressure decrease in the upstream portion of the pump tubing │
│    segment during rotation of the motor unit to obtain a running strain. │
└─────────────────────────────────────────────────────────────┘
                              │
                              ▼
┌─────────────────────────────────────────────────────────────┐
│  Subtract running strain from stopped strain to obtain delta strain which is │
│        inversely proportional to the volume infused by the pump.       │
└─────────────────────────────────────────────────────────────┘
                              │
                              ▼
┌─────────────────────────────────────────────────────────────┐
│        Compare delta strain to empirically determined strain and threshold.        │
└─────────────────────────────────────────────────────────────┘
                              │
                              ▼
┌─────────────────────────────────────────────────────────────┐
│                  If delta strain does not exceed threshold.                 │
└─────────────────────────────────────────────────────────────┘
                              │
                              ▼
┌─────────────────────────────────────────────────────────────┐
│   If delta strain is low, i.e. similar to empirically determined strain - fluid is of │
│       low viscosity and there are no significant partial occlusions.  No       │
│    modification made to number of rotations during each period during which    │
│                            motor is running.                            │
└─────────────────────────────────────────────────────────────┘
                              │
                              ▼
┌─────────────────────────────────────────────────────────────┐
│  If delta strain is high but does not exceed threshold - fluid is highly viscous │
│    or a partial occlusion is present. Number of rotations during each period    │
│       the motor is running is increased proportional to the delta strain to      │
│              increase fluid output to achieve desired fluid flow.               │
└─────────────────────────────────────────────────────────────┘
                              │
                              ▼
┌─────────────────────────────────────────────────────────────┐
│    If delta strain is at or above threshold - occlusion or extreme viscosity     │
│   prevents proper adjustment of fluid output by adjusting period of rotation   │
│    of the motor unit. Motor unit is stopped and warning signal is sent         │
│                 indicating lack of fluid flow into the pump.                    │
└─────────────────────────────────────────────────────────────┘
```

*Fig. 7*

METHOD FOR MONITORING VISCOSITY AND OCCLUSIONS IN AN ENTERAL FEEDING PUMP DELIVERY

RELATED APPLICATIONS

This is a continuation-in-part application of U.S. Pat. No. 5,514,102 (U.S. patent application Ser. No. 08/435,714) for a Pressure Monitoring Enteral Feeding System and Method, filed May 5, 1995 and issued May 7, 1996.

BACKGROUND OF THE INVENTION

The present invention relates to systems for feeding solutions to patients, and in particular to an enteral feeding system using pressure sensors to ensure that delivery of the solution by an enteral feeding pump is within desired parameters. Specifically, the invention relates to the use of pressure sensors to determine the viscosity of fluids and the presence of occlusions in the delivery set which passes through an enteral feeding pump, and for a method of compensating for delivery volume changes due to partial occlusions or fluid viscosity.

An enteral feeding system is used to provide nutrient solutions to patients who, for one reason or an other, are unable to eat for themselves. Such a system typically includes a pump which is attached to an input tube connected to a supply container and to an output tube which is connected to a patient. The pump draws nutrient solution from the supply container and delivers the solution to the patient. By adjusting the number of rotations of the motor in the pump, an enteral feeding pump can adjusts it output to deliver a predetermined amount of nutrient solution (or even medication) at a desired rate. The use of various types of enteral feeding systems is well known in the medical arts.

A significant problem with currently available enteral feeding systems, is that the intake and output tubes may become occluded. Occlusion can occur, for example, if a fibrous substance is included in the solution and somehow combines to interfere with flow through the tube. Occlusion can also occur if a tube is bent sufficiently to interfere with flow therethrough, or if a roller clamp (as is commonly used for intravenous applications) is not sufficiently loosened.

If the intake tube becomes occluded, insufficient solution may be supplied to the pump, and thus to the patient. If the output tube becomes occluded, the flow of solution may be blocked, or the solution may be delivered at unusually high pressures. Additionally, medical personnel may fail to notice that the supply container is out of solution, or may not properly mount the intake and/or output tubes in the pump, thereby preventing the proper amount of solution from being delivered to the patient. Any of these scenarios can have tragic consequences if medical personnel are not alerted in time.

Yet another concern with enteral feeding systems is that of viscosity of the solution and viscosity changes as a container full of solution is pumped to a patient. Knowing the viscosity of the fluid being pumped through the enteral feeding system is important because different viscosities are pumped at different rates by the enteral feeding pump. For example, a lower quantity of a highly viscous solution will be pumped by a given number of rotations of the enteral feeding pump than will be fed to the patient when the solution is of low viscosity. Thus, unless the pump is able to accurately determine and compensate for viscosity changes in the solution, it is difficult to know exactly how much of the solution has been fed to the patient.

To overcome these concerns, there is a need for a system and method for determining discrepancies due to occlusions, viscosity including changing viscosity) and/or improper fitting of pumps and intake/output tubes so that patients will not be endangered, and so that the proper amount of fluid will be delivered to the patient.

OBJECTS AND SUMMARY OF THE INVENTION

It is an object of the present invention to provide an enteral feeding system including an enteral feeding pump with at least one sensor to ensure that intake and output tubes are properly positioned within the feeding pump.

It is another object of the present invention to provide an apparatus and a method for monitoring fluid flow through an enteral feeding system to determine the amount of fluid being delivered to the patient.

It is another object of the present invention to provide an apparatus and method for determining the effect of viscosity and occlusions on flow through the enteral feeding system to more accurately determine the amount of fluid delivered to the patient.

It is yet another object of the present invention to provide an apparatus which monitors viscosity and occlusions in the delivery set and indicates when viscosity changes or occlusions occur.

Yet another object of the present invention is to provide such an apparatus which compensates for the viscosity changes or occlusions to maintain consistent fluid output by the enteral feeding system.

It is still another object of the present invention to provide an enteral feeding system including an enteral feeding pump having upstream and downstream sensors for determining the extent of occlusion of the inlet and/or output tubes connected to the pump.

It is a further object of the present invention to provide an enteral feeding system having sensors on the intake and output tubes so as to determine location of an occlusion in the event occlusion occurs.

It is still a further object of the present invention to provide an enteral feeding pump incorporating such sensors which may be used with conventional disposable delivery sets.

The above and other objects features and advantages of the present invention will become apparent in an enteral feeding system including a pump which has a motor in communication with an intake tube for receiving a nutrient solution from a supply container and an output tube for delivering solution to the patient. The enteral feeding system also includes a pair of pressure sensors placed along the delivery set for monitoring the tubes and determining if there is an occlusion or a viscosity change in the fluid within the system.

In accordance with one aspect of the invention, a proximal pressure sensor is placed along the intake tube and a distal pressure sensor is placed along the output tube so as to monitor the pressure in each tube and thereby determine if either tube has an occlusion, and to determine if either tube is not properly attached to the enteral feeding pump.

In accordance with another aspect of the invention, the pressure changes between periods when the motor is running and periods when the motor is not running is used to determine whether occlusions are present, and whether viscosity changes have occurred in the fluid passing through the delivery set. The information obtained from the pressure sensors regarding viscosity changes or occlusions is then used to adjust the number of rotations during a period wherein the pump moves fluid to thereby maintain a desired dose of the fluid. Thus, for example, if a highly viscous fluid is detected by the pressure sensors, the time period that the pump runs during each cycle typically will be increased, as the greater the viscosity of the fluid, the lower the volume that will be moved by each rotation of the pump.

In accordance with another aspect of the invention, the alternating current output of the pressure sensors caused by changing tension on the tubing is monitored so as to indicate proper operation of the pressure sensors.

BRIEF DESCRIPTION OF THE DRAWINGS

The above and other objects, features and advantages of the invention will become apparent from a consideration of the following detailed description presented in connection with the accompanying drawings in which:

FIG. 1 shows a bottom fragmented view of an enteral feeding system including an enteral feeding pump connected to intake and output tubes;

FIG. 2 shows a top fragmented view of an enteral feeding system including an enteral feeding pump connected to intake and output tubes;

FIGS. 5 and 5A show a preferred embodiment of an enteral feeding pump made in accordance with the principles of the present invention, the pump including a cover to hold the inlet and output tubes in a desired position;

FIG. 7 provides a diagram of the method used to determine fluid viscosity and occlusions in the intake tubing and to adjust pump output to compensate for decrease fluid flow through the pump.

DETAILED DESCRIPTION

Figure 3A:
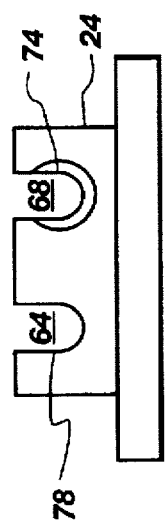
FIG. 3A shows an end view of the enteral feeding pump of the present invention taken along the line A.

Reference will now be made to the drawings in which the various elements of the present invention will be given numeral designations and in which the invention will be discussed so as to enable one skilled in the art to make and use the invention. Referring to FIG. 1, there is shown a bottom view of an enteral feeding system, generally indicated at 4, having a delivery set 8 including an intake (upstream) tube 10 and an output (downstream) tube 14 connected together by a pair of connectors 18 and a pump tubing segment within an enteral feeding pump 20. The position of the pump tubing segment disposed inside of the pump 20 is represented by the dashed lines 16. Typically an opposing end (not shown) of the intake tube 10 would be connected to a supply container (also not shown) and an opposing end (not shown) of the output tube 14 would be attached to a patient so as to deliver solution provided by the pump 20.

The enteral feeding pump 20 includes a housing 24 with a conventional motor unit, generally indicated at 28. The motor unit 28 includes a rotor 30 with a plurality of peristaltic rollers 34 disposed about an exterior of the rotor to move liquid through the enteral feeding pump 20. The rotor 30 is connected by a shaft 32 to a motor (not shown). The section 38 of the pump tubing segment 16 is disposed about the rotor 30 and rollers 34 and is usually made of a flexible silicone material. Rotating the rotor 30 in the direction indicated by the arrows directionally squeezes the tube section 38 and causes solution to be pushed out of the enteral feeding pump and through the output tube 14. Typically, each rotation of the rotor will move about ¼ ml of solution. However, viscosity changes and partial occlusions in the output tube 14 and, most particularly, in the intake tube can reduce the amount of fluid moved by each rotation of the rotor 30.

Also shown in FIG. 1 is an air detector 40 provided in a proximal position (upstream) from the motor unit 28 along the intake tube 10 to warn medical personnel of an empty supply container. The above described elements of an enteral feeding pump are generally known to those skilled in the art. Of course, the air detector could be disposed on the downstream portion of the tubing segment 16 as shown in U.S. Pat. No. 5,514,102.

In addition to these elements, the enteral feeding pump 20 of the present invention includes a pair of pressure sensors 50. In a preferred embodiment, two pressure sensors 50a and 50b are disposed along the pump tubing segment 16 adjacent the intake/output tubes, 10 and 14 in order to 1) ensure that the tubes are properly mounted in the pump 20; 2) monitor any changes in viscosity which are significant enough to alter the amount of liquid moved by each rotation or partial rotation of the rotor 30; and 3) detect any occlusions in the intake tube 10 or the output tube 14 of the delivery set 8. A retention plate 54 (FIG. 1) is attached to the housing 24 by a screw 58 to hold the pressure sensors 50a and 50b in place. As will be appreciated, if the sensors are not securely held, any readings obtained will be unreliable.

As the pump 20 operates, the motor unit 28 mechanically blocks the tube section 38 and pushes fluid within the tube toward the output tube 14. During this process, the pump tubing segment 16 stretches and contracts due to rotation of the rotor 30 and due to the response of liquid within the pump tubing segment to the suction created by each rotation of the pump. The stretching and contracting can be measured by the pressure sensors. This is an expected signal and its absence is interpreted by a control processor (discussed below) as a failure of the corresponding sensor.

While discussed herein as a pump tubing segment, the tubing passing through the pump 20 could be an intake line and an output line connected together. In such a situation, each would preferably be made of the same materials as pump tubing segment 16.

In FIG. 2, there is shown a fragmented top view of the enteral feeding system 4. As is apparent, the pump tubing segment 16 is attached to the intake tube 10 and the output tube 14, and extends along the housing 24 to a position about the motor unit 28. The underside of the housing 24 has channels 64 and 68, respectively, for receiving the pump tubing segment 16 so that it is disposed adjacent to the respective pressure sensors, 50a and 50b.

In FIG. 2 there is also shown a void 70 formed in the channel 64 designed to receive an occluding mechanism, such as a pinch clip occluder (not shown), which may be used with the pump tubing segment 16 to selectively prevent solution from flowing through the pump tubing segment until the occluding mechanism has been released. (An example of such a pinch clip occluder is contained in U.S. Ser. No. 08/410,912 filed on Mar. 27, 1995, and which is expressly incorporated herein). Thus, unless the pump tubing segment 16 has been properly fitted into the channel 64 so that the occluding mechanism properly nests within void 70 and the pump door (not shown) can close properly, solution will not flow through the pump 20. This is important because medical personnel occasionally fail to properly thread the pump tubing segment 16 through the enteral feeding pump 20 or to close a roller clamp, etc., prior to opening the pump door.

Failure to properly connect the system 4 can result in a situation known as free flow wherein the rate at which solution is supplied to the patient is not dependant on the motor unit 28, but rather on the force of gravity and on the amount of solution in the supply container. If the supply container is disposed above the patient, a much greater quantity of solution will usually enter the patient than would have had the pump tubing segment 16 been properly mounted in the channels 64 and 68 of the pump 20 so that flow through the section 38 was controlled by the motor 28. The large infusion of solution can cause serious complications for the patient, and occasionally can result in death. By using an occlusion mechanism which is released by fitting it within the void 70 or some similar arrangement, this free flow condition can be avoided.

The pressure sensors 50a and 50b compliment this feature by ensuring that the pump tubing segment 16 is properly positioned within the channels 64 and 68, and that fluid is flowing through the tubing segment properly. The risk of using an occluding mechanism which is biased in a closed position is that fluid flow through the device will be halted if the clamp has not been moved into an open position. This can prevent fluid flow even if the remainder of the delivery set is properly mounted, and can harm the patient if undiscovered. In such a situation, the pressure sensors 50a and 50b will indicate an occlusion, as no fluid will be flowing though the pump tubing segment 16. The occlusion alert warns medical personnel that the pump 20 should be checked—thereby allowing the medical personnel to determine that the pump tubing segment 16 has not been properly loaded and the feeding or other solution is not flowing therethrough.

Referring now to FIG. 3A, there is shown an end view of the pump housing 24 taken along line A of FIGS. 1 and 2. The housing 24 has a pair of openings 74 and 78 which lead into channel 68 and 64, respectively, which are positioned generally parallel to one another. When the intake tube 10 and the output tube 14 (FIGS. 1 and 2) are nested into the channels 64 and 68, they are held by the sides of the openings 74 and 78.

Figure 3B:
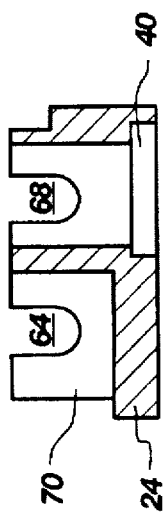
FIG. 3B shows a cross-sectional view of the enteral feeding pump of the present invention taken along the line B.

In FIG. 3B, there is shown a cross-sectional view of the housing 24 taken along the line B of FIGS. 1 and 2. The air detector 40 is disposed about channel 68, and the void 70 is formed about channel 64 as was discussed with respect to FIG. 2.

Figure 3C:
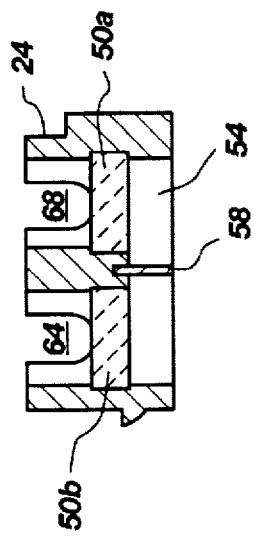
FIG. 3C shows a cross-sectional view of the enteral feeding pump of the present invention taken along the line C.

Referring to FIG. 3C, the pressure sensors 50a and 50b extend up into the channels, 68 and 64 respectively, so that sensor 50b will contact the pump tubing segment 16 near the output line 14 (FIGS. 1 and 2) and sensor 50a will contact the pump tubing segment near intake line 10 (FIGS. 1 and 2). The sensors 50a and 50b press up on the pump tubing segment 16 sufficiently that they can determine the pressure which exists in the tube. As will be discussed in additional detail with respect to FIGS. 5 and 6, the tubes can also be held down firmly against the sensors by a cover.

A decrease in the pressure on sensor 50a indicates that pressure has fallen in the intake tube 10. This indicates that either the intake tube 10 is occluded on an upstream side of the sensor, or that the fluid viscosity or head height has decreased. If the air detector 40 indicates a bubble and the sensor 50a indicates low pressure, then the supply container typically will have run dry.

The extent of pressure change detected by the sensor 50a usually indicates whether there is an occlusion or low fluid level. For example, with each rotation of the motor unit (not shown in FIG. 3C), the intake tube 10 will undergo a momentary partial collapse, i.e. a decrease in outward pressure within the tube. The partial collapse is caused by the suction of the motor unit moving a portion of fluid. By monitoring the pressure change which occurs during this period, the pressure sensors and related circuitry of the enteral feeding pump can determine whether the viscosity of the solution within the tubing segment has changed, or whether the tubing segment is partially or completely occluded. With the information, the enteral feeding pump can then either make corrective adjustments to compensate for the partial occlusion or viscosity change, or can indicate that the occlusion is extreme enough that it cannot be remedied. If the occlusion, etc., cannot be remedied by corrective adjustments, the pump will shut down and send a warning signal to medical personnel.

In contrast to monitoring for pressure decreases in pressure sensor 50a, an increase in the pressure on sensor 50b indicates that there is a partial or complete occlusion in output line 14. Thus, by observing the output of each sensor 50a and 50b, medical personnel can be assured that solution is being delivered to the patient at the proper pressure. Those skilled in the art will recognize that each rotation of the motor unit will cause temporary increases in pressure on sensor 50b and decreases on sensor 50a. Part of the change in pressure occurs because of changes on the tension of the tubing. Rather than filtering out this component, it is monitored to ensure that the pressure sensors 50a and 50b are functioning properly. Additionally, rather than ignoring the sharp peak caused by each movement of the rotor 30, the entire curve is monitored and an average taken. If the average exceeds a predefined threshold, an alarm is activated. Such a method, prevents a momentary occlusion alarm as may be caused by a patient's movement.

As was discussed regarding FIG. 1, the sensors 50a and 50b are held in place by the retention plate 54 which is held to the housing 24 by screw 58. A silicone boot (not shown) may be included for sealing and holding the sensors 50a and 50b in the appropriate place. In the event a pressure sensor 50a or 50b malfunctions, the plate 58 (and boot) can be removed by unscrewing screw 58, thereby enabling the sensor to be replaced.

Figure 4A:
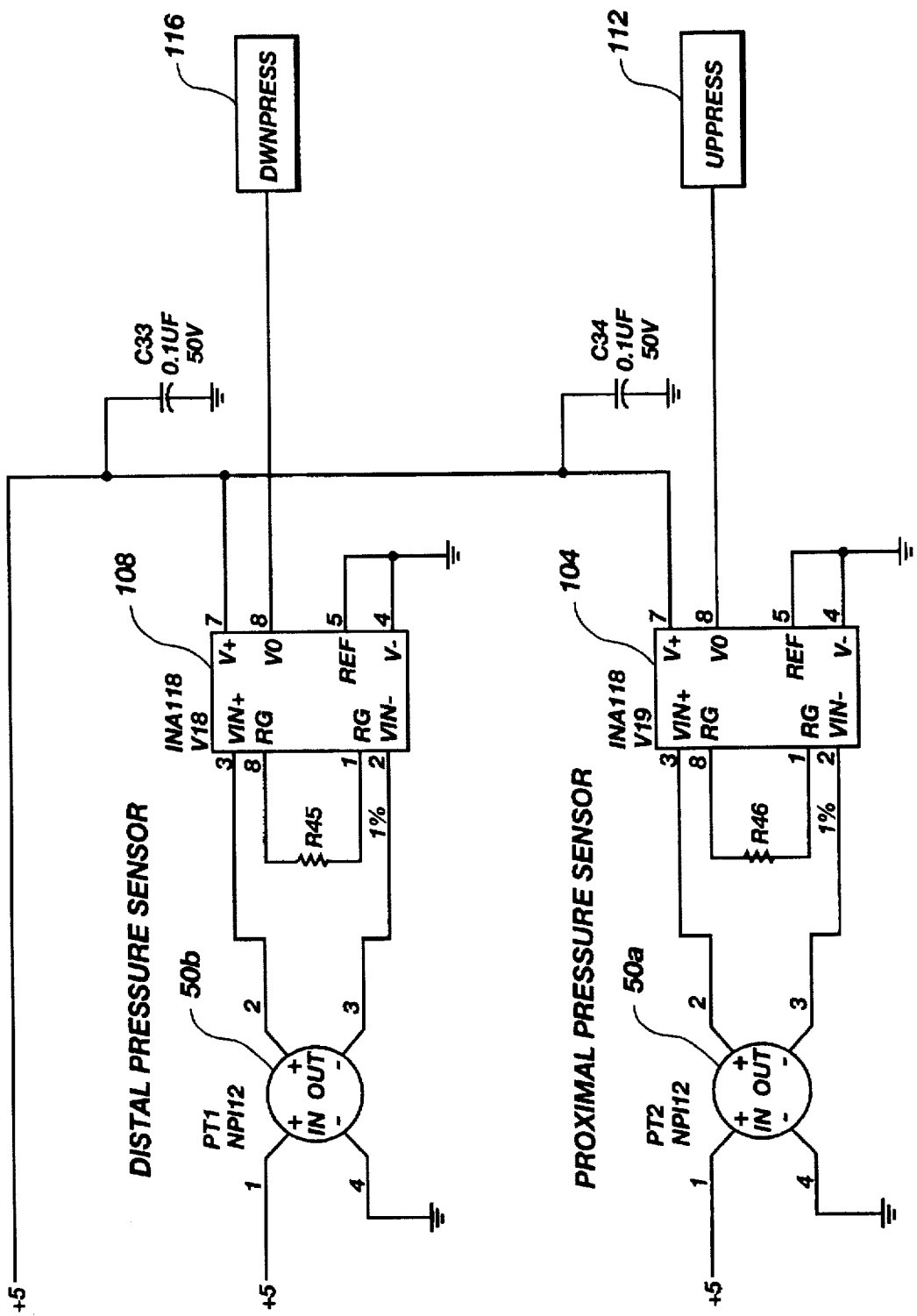
FIGS. 4A and 4B are schematics of the circuitry used to monitor the pressure of solution passing through the intake and output tubes.
Figure 4B:
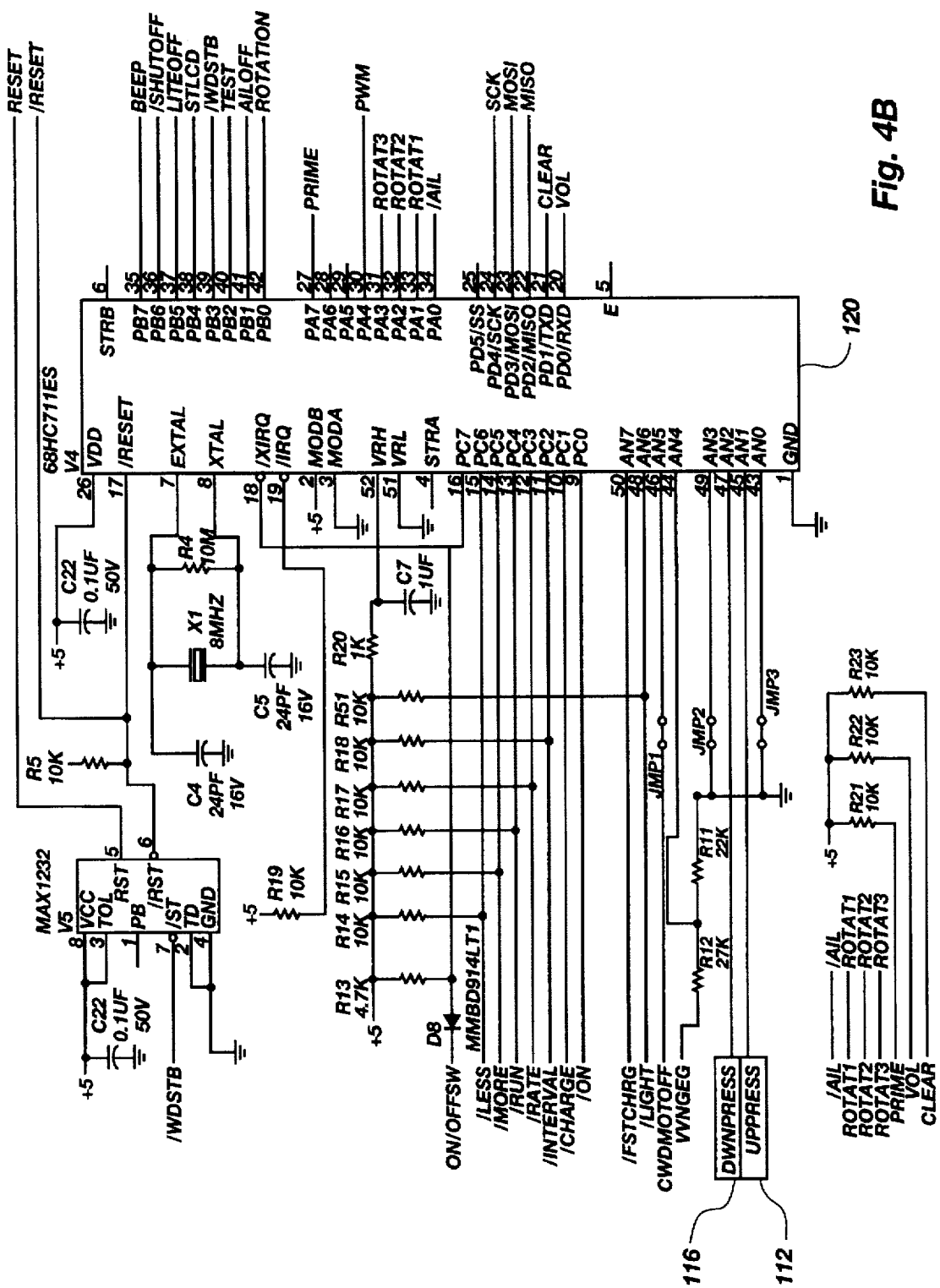

Referring now to FIG. 4A, there is shown a schematic view of the circuitry for the pressure sensors 50a and 50b. Each sensor 50a and 50b is connected to a respective preprocessor, 104 and 108. The preprocessors 104 and 108 are, in turn, connected to input/output lines 112 and 116 which communicate with a control processor 120 which is shown in FIG. 4B. By monitoring the readings from the pressure sensors 50a and 50b and preprocessors, the control processor 120 can determine whether an occlusion exists, either upstream or downstream, whether the viscosity of the solution pumped through the tubing segment 16 has changed, and whether the delivery set 8 has been loaded properly. It should be appreciated by those skilled in the art that combined circuitry could be used to monitor the pressure sensors and other dynamics of the system, such as the position of the rotor 30 (FIGS. 1 and 2) and the speed at which it rotates. By incorporating all of this information, a single set monitor could be used to supply all information needed about the enteral feeding system 4 and to allow the user (or the system itself) to modify the dynamics of the system as needs change.

Additionally, the control processor could be preprogrammed to control the rotor in response to information obtained from the sensors 50a and 50b. Thus, for example, if an occlusion were detected downstream from the motor unit 28, the control processor 120 may stop operation of the rotor and emit a warning to medical personnel that the pump has shut down due to an occlusion. Likewise, changes in upstream pressure sensed by the sensors 50a and 50b may be used by the control processor to control the rotation rate or period of time during which the motor unit rotates to ensure consistent delivery of the fluid.

Referring now to FIGS. 5 and 5A, there is shown a top view and an end view of an enteral feeding pump 200. The pump includes a motor unit 204 and all of the other features discussed in FIGS. 1 and 2. The primary difference between the pump 200 in FIG. 5 and the pump 20 in FIGS. 1 and 2, is that pump 200 has a cover 208 for ensuring that the pump tubing segment 216 is properly positioned in the channels 220 and 224, and that the pump tubing segment is in firm contact with the sensors 230a and 230b.

The cover 208 is attached to a base portion 240 of the pump 200 by one or more hinges 244 so as to enable the cover to be rotated between an open position, in which the channels 220 and 224 are accessible, and a closed position in which they are not. The cover 208 has a pair of projections 250 and 254 which extend downwardly into the channels 220 and 224 so as to hold the pump tubing segment 216 firmly against the sensors 230a and 230b. Having the tubes 210 and 214 in place so that the pump tubing segment 216 is in firm contact with the pressure sensors 230a and 230b allows for more accurate readings.

The cover 208 also has a clip portion 260 which extends along the base portion 240 to a small groove 264 formed therein. The clip portion 260 of the cover 208 is typically resilient, and a flange 268 extending from the clip portion will nest in the groove 264 so as to hold the cover in place. To release the cover 208 and provide access to the channels 220 and 224 in the base portion 240, the clip portion 260 need only be bent so that the flange 268 does not nest in the groove 264. The cover 208 may then be pivoted out of the way. When the tubes 210 and 214 have been adjusted, or replaced, etc., the cover 208 need merely be rotated into the position shown in FIG. 5, and a small amount of force applied until the flange 268 nests in the groove 264 to hold the cover shut. Once the tubes 210 and 214 are placed in the channels 220 and 224, and the cover 208 is shut, the tubes are locked in place, and may only be removed by opening the cover. Preferentially, the cover 208 is attached to the base portion 204 in such a way that it may be replaced if damaged.

Figure 6:
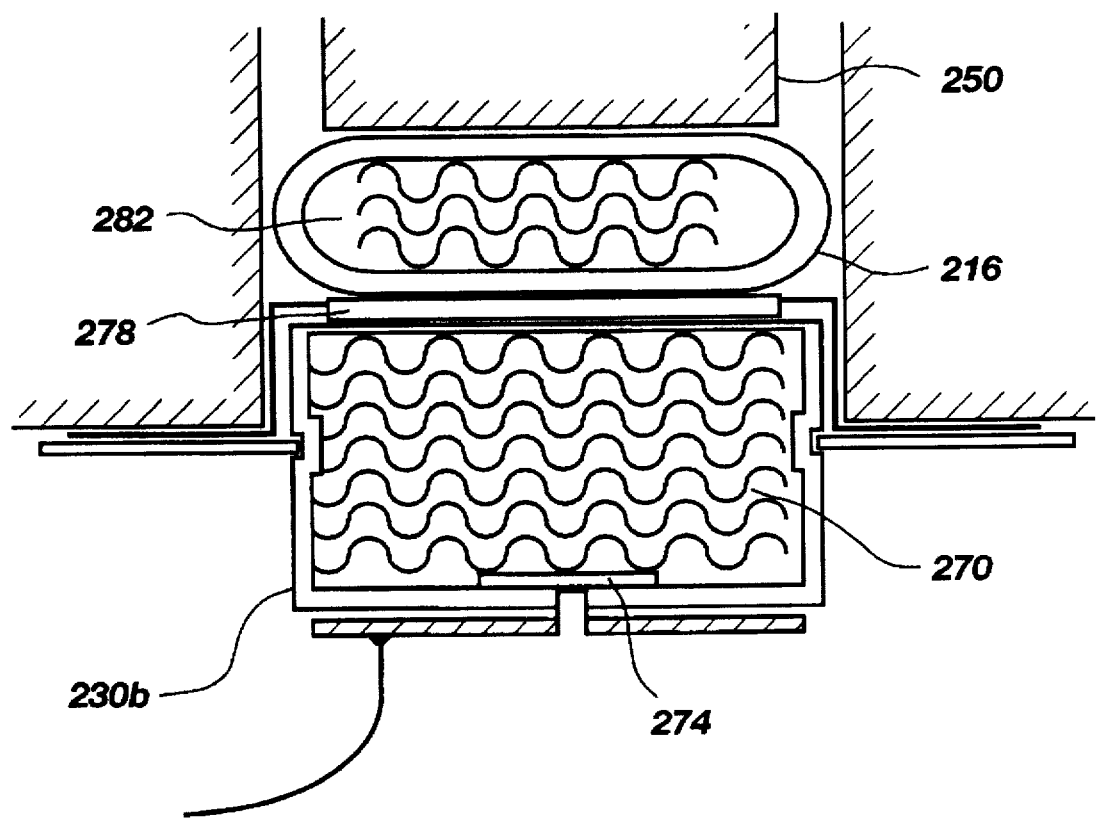
FIG. 6 shows a fragmented, cross-sectional view of the pressure sensor with a tube mounted adjacent thereto.

Referring now to FIG. 6, there is shown a close-up, fragmented cross-sectional view of a pressure sensor 230b and the surrounding area. The pressure sensor includes an oil filled reservoir 270 and a pressure sensor chip 274. A silicone gasket 278 fits between the pressure sensor 230b and the tube 216. The tube 216 is held in place by the projection 250. The partially collapsed tube 216 will exert pressure on the sensor 230b. When there is fluid 282 in the tube 216, increases in fluid pressure will be detectable by the pressure sensor 230b which communicates the increase to the control processor 120 (FIG. 4B). If the delivery set 8 (FIG. 1) were not loaded properly, the pressure sensor 230b would send a signal to the sensor chip 274 representing an insufficient pressure condition. The control processor 120 would then send a user identifiable signal indicating that the delivery set is not properly loaded. If an occlusion occurs downstream, the sensor 230b will send a signal to the control processor 120 (FIG. 4B) indicating the existence of an occlusion. While the sensor 230b shown in FIG. 6 is believed to be the preferred embodiment, those skilled in the art will be aware of numerous other types of pressure sensors which may be used to achieve the functions of the present invention.

As was mentioned previously, the pressure sensors 50a and 50b, or 230a and 230b can be used to determine both changes in viscosity in the solution being pumped through the tubing segment 16, and to determine the presence of occlusions. In FIG. 7, there is shown a diagram of the method used to determine problems with fluid viscosity and occlusions in the intake or upstream tubing and to adjust pump output to compensate for decreased fluid flow through the pump. Thus, when discussing the pressure sensor with respect to FIG. 7, the reference will be to the upstream sensor unless indicated to the contrary. For ease of reference, the embodiment shown in FIGS. 1 through 3C will be used for the discussion.

When fluid is passed through the pump 20, each rotation of the rotor 30 will cause a temporary negative pressure within the proximal portion pump tubing segment 16 adjacent the rotor 30 as the fluid moved by the pump 20 must be replaced. The ability of the fluid to flow into the vacated area and fill the vacuum is related both to its viscosity and to the presence of any occlusions which would inhibit fluid flow into the pump. Highly viscous fluids and occlusions cause a lag in fluid replacement due to the flow resistance.

High viscosity and occlusions also have an effect on the amount of fluid which each rotation or partial rotation of the rotor 30 and motor unit 28 can move. Higher viscosities and/or partial occlusions, result in less fluid pumped by each rotation of the rotor 30. Therefore, to determine the amount of fluid which is actually being delivered to the patient, the viscosity of the fluid and/or the presence and extent occlusions must be known. By correlating this information with the rotation rate of the rotor, the pump can adjust to maintain a desired output.

To determine whether viscosity or occlusions are inhibiting fluid flow through the pump 20, the force or strain exerted on the pressure sensors by the tubing can be used. The strain stopped, i.e. the amount of strain on the tubing when the rotor is not rotating provides a reference point for determining the viscosity of the fluid and/or the presence of occlusions. As will be apparent from the discussion with respect to FIGS. 1 through 3C, the lack of any strain on the tubing segment 16 will indicate that no fluid has been allowed into the tubing. This may be either due to a complete occlusion, or due to a pinch clip occluder disposed in the void 70 which has not been released. Either way, the pump 20 will send a warning signal indicating that there is no fluid flow into the pump 20.

If a "strain stopped" is present, the circuitry (FIGS. 4A and 4B) of the pump will store the value obtained from the pressure sensor 50a. Once the rotor 30 rotates, the pressure sensor 50a and any circuitry determines the strain running, i.e. the strain within the proximal portion of the tubing segment 16 as the motor unit 28 rotates the rotor 30. Because the rotation of the rotor 30 draws off fluid, the strain running will be below that of the strain stopped. The extent of the drop indicates the extent of any occlusion, or the viscosity of the fluid: the lower the strain running, the higher the viscosity or the more complete the occlusion.

The circuitry of the pump 20 records the strain running and subtracts it from the previously recorded strain stopped. If the resulting change or delta strain is small, then no modifications are necessary. What is determined to be small is usually figured on the basis of empirically derived levels for changes in strain using a low viscosity fluid such as water. As the pump 20 is calibrated, the pump is programmed to pump a given amount of fluid assuming an occlusion free delivery set and a viscosity for the fluid similar to water. If the viscosity of the fluid actually pumped is higher than water, changes must be made to the number of rotations allowed during each "running" period. This can be accomplished by increasing motor speed during the running period, or by lengthening the running period to allow more rotations while keeping the rotation rate constant. By using the pressure sensor 50a, the pump 20 can continually monitor the solution being pumped to ensure that any changes in viscosity or any occlusions are accounted for by adjusting the number of rotations of the rotor 30 during each running time.

If a low delta strain is indicated, then no corrective measures must be undertaken. The low delta strain indicates that no significant occlusions are present, and that the viscosity level is in harmony with the control viscosity used for calibrating the pump. Therefore, the number of rotations of the rotor 30 within each running period will remain constant.

If a high delta strain is indicated, then some corrective measures must be taken to ensure that the proper dose of fluid is being delivered during each period during which the motor unit 28 is running. Within certain parameters, this may be accomplished by simply increasing the number of rotations of the rotor 30 during each running period to compensate for the decreased volume pumped. It is presently believed that the increase in rotations necessary to compensate for the occlusion or higher viscosity is proportional with the delta strain with an empirically defined range. Within this range, the pump 20 considers the change in strain to be a "viscosity" change, and alters the rotation cycles during the running period to adjust. Thus, for example, if the rotor 30 is programmed to take six steps, each step typically being one-third of a rotation, during the running period, the circuitry may indicate to the motor unit 28 to extend the running period so that the rotor 30 takes seven steps before the running period is terminated.

However, at a certain threshold, increasing the number of rotor 30 revolutions for each running period will no longer compensate for the occlusion or viscosity. At this threshold, the pump's analysis indicates an "occlusion" or blockage of the tubing. This will typically occur at a nearly complete occlusion, although it could also occur with an extremely viscous solution. When the delta strain exceeds the threshold, the pump is programmed to stop rotation of the motor unit and to send a warning signal to medical personnel that no fluid is flowing into the pump. The medical personnel can then evaluate the delivery set to determine the reason that fluid flow has ceased.

The exact level at which the threshold is set will depend both on the particular pump being used and the desired sensitivity. For example, with the present invention, the threshold may be set at 8 p.s.i. for use with solutions containing medications, and at some higher figure when the pump is being used exclusively for feeding. In light of the present disclosure, those skilled in the art will be able to readily determine desirable thresholds for different types of pumps.

Figure 8:
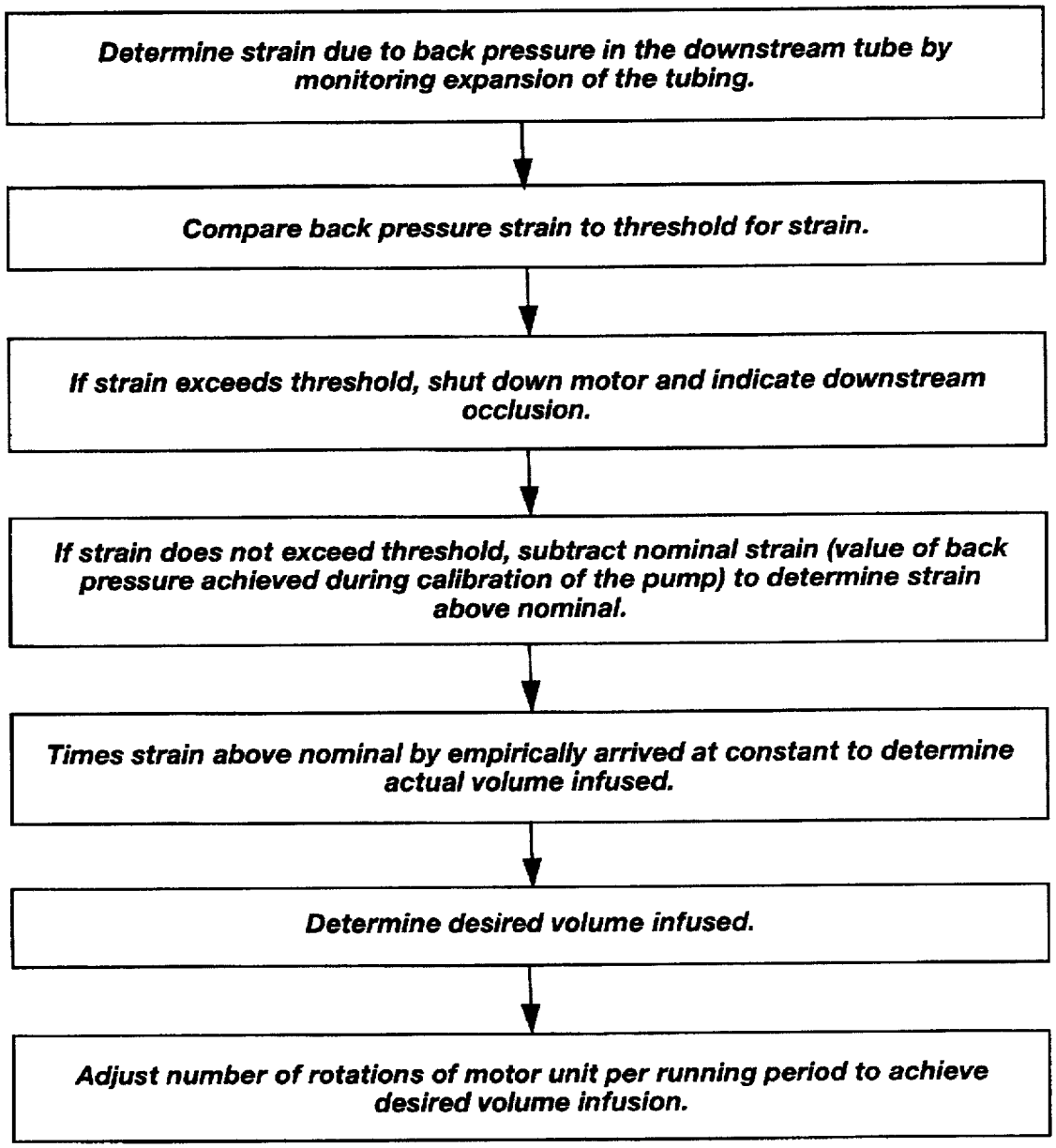
FIG. 8 shows a diagram of the method for adjusting the pump to compensate for back pressure and occlusions in the output tube.

FIG. 8 shows a diagram of the method for adjusting the pump to compensate for factors in the output tube which interfere with the infusion of fluid into a patient. Those skilled in the art will appreciate that occlusions or other interference in the downstream tubing can also significantly interfere with the volume which is actually delivered to the patient, as opposed to the volume which the medical personnel believes is being delivered. The higher the back pressure, the less volume will actually be infused into the patient from a given number of rotor 30 rotations.

Back pressure can be caused by several situations. For example, a partial occlusion may develop in the output tube 14, thereby inhibiting fluid flow. Additionally, the physical position of the patient may cause back pressure by bending the output tube and restricting flow therethrough.

In order to ensure that a desired volume of fluid is being infused by the enteral feeding pump, one must determine the actual infusion volume and then modify the number of rotations of the rotor 30 during the running period so that the actual infusion volume matches the programmed or desired infusion volume.

To monitor the effect which back pressure is having on the output tubing, the pressure sensor 50b monitors strain, i.e. expansion pressured on the tubing segment 16 adjacent the pressure sensor. If the back pressure strain is above a predetermined threshold, such as 12 p.s.i., the circuitry (FIGS. 4A and 4B) in the pump 20 will indicate that an occlusion is present. The circuitry will then shut down the motor unit 28 and indicate a downstream occlusion.

If the strain readings obtained by the pressure sensor 50b are below the threshold, then it is important to determine what volume of fluid is actually being infused by the pump 20. This is achieved by subtracting a nominal strain value for back pressure within the pump from the actual back pressure strain obtained by pressure sensor 50b. The nominal value is typically achieved during calibration of the pump using water as the fluid and providing no resistance in the tube to flow. Thus, the nominal back pressure will typically be near zero.

The excess strain, i.e. the actual back pressure strain above the nominal strain value is then multiplied by an empirically arrived at constant to achieve the actual infusion rate of the fluid passing through the pump. With the actual volume infused determined, the circuitry then accesses the desired volume entered by the medical personnel. The circuitry then increases the number of rotations (or partial rotations) during each running period to compensate for the sensed back pressure to achieve the desired flow rate.

While presented herein separately, those skilled in the art will appreciate that the pump 20 simultaneously adjusts for pressure concerns on both sides of the motor unit 28. The adjustments are a dynamic process which continue throughout the delivery process, as occlusions and viscosity changes can alter the volume infused in a very short period of time.

EXAMPLE 1

Thus, for example, an operation of the pump of the present invention may function as follows. The desired rate of infusion and the volume of fluid (dose) to be infused are entered by medical personnel when setting up the pump, the rate is 180 ml/hr and the dose is 180 ml. This equates to a total infusion time of one hour. The pump then breaks this down into a finite number of smaller running periods/feeding intervals. The pump actively monitors viscosity and downstream back pressure while running and can compensate nu numerous times during the same feeding interval for accurate delivery. The adjustments for upstream occlusions/viscosity changes and for downstream back pressure are again segmented for ease of reference. The accumulative results conclude the example.

Viscosity

The upstream pressure sensor 50a initially monitors strain while the motor unit 28 is not running and receives a strain stopped reading of 5 psi. Once the motor unit 28 begins to rotate the rotor 30, the pressure sensor 50a takes a reading for strain running and records 3.49 psi. Subtracting the strain running from the stain stopped, the pump 20 obtains a delta strain of 1.51 psi. From the magnitude of delta strain the solution is considered either a low or high viscosity solution.

Utilizing empirical values, the delta strain is first multiplied by a constant and then summed with a volume representative of the condition when the delta strain is equivalent to zero. For the example given, a low viscosity solution is recognized and the pump delivery is equated to 4 revolutions during each running period/feeding interval.

If the viscosity changes during this same feeding interval, the pump will detect this and compensate. The same reading of the strain with the motor stopped of 5 psi is maintained. The pressure sensor takes a new reading for strain running and records 1.57 psi. Subtracting the strain running from the strain stopped, the pump 20 obtains a delta strain of 3.43 psi. The pump recognizes that the solution is now of higher viscosity and increases the motor rotations from 4 to 4.84 within each running period/feeding interval.

DOWNSTREAM BACK PRESSURE (Partial Occlusion)

Turning to the downstream back pressure, the pressure sensor 50b obtains a stain reading of 7 psi. Subtracting the nominal strain value of 0 psi from he back pressure strain reading, an excess strain value of 7 psi is obtained.

Multiplying the excess strain of 7 psi by a constant obtained empirically (depending upon the pump configuration), the pump 20 determines that the number of rations of the rotor 30 during the running period/feeding interval should be increased from 4.84 to 5 in order to deliver the solution at the desired rate of 180 ml/hr.

Therefore, the net effect of the viscosity and back pressure amounts to an increase of motor rotations from 4 to 5 (an increase from 4 To 4.84 for viscosity, and an additional increase of 0.26 for back pressure).

Thus, by modifying the number of rotations, the pump 20 is able to achieve the desired infusion volume, even if occlusion, viscosity changes or back pressure changes during the infusion period. If the occlusion, viscosity or other causes of back pressure is too extreme to be remedied by modifying pump speed, the pump will shut down and indicate to the medical personnel that the tubing or the solution must be changed.

One additional advantage of the present invention is that the pump described avoids the necessity of having a suspended supply container. To ensure a proper flow rate, many prior art pumps have a drip chamber disposed below the supply container. An optical sensor is used to ensure that a desired number of drops of solution pass within a given period. Such an arrangement, however, is cumbersome because the supply container must always be elevated/suspended to provide proper flow through the drip chamber.

In contrast, the present invention allows the use of a supply container which is neither suspended nor elevated. Rather than relying on the drip chamber, the pressure sensors of the present invention can be combined with an accurate method for determining the position and rotation rate of the rotor, such as disclosed in U.S. patent application Ser. No. 08/435,735 to accurately determine fluid flow through the pump.

In the manner set forth above, an Enteral Feeding System and Method is disclosed including an intake tube, an output tube and a pump tubing segment, along which an enteral feeding pump is disposed. A pair of pressure sensors are provided to ensure that the pump is operating properly, and the intake and/or output lines are not occluded. Those skilled in the art will recognize numerous other modifications which could be made while remaining within the scope and spirit of the invention. The appended claims are intended to cover such modifications.

What is claimed is:

1. A method for obtaining a desired output from an enteral feeding pump having a motor unit attached to a rotor to rotate the rotor a number of rotations during a running period and to not rotate the rotor during a stopped period, and a tubing segment extending around the rotor so as to have a proximal portion and a distal portion, the method comprising:
   a) disposing a pressure sensor in contact with the proximal portion and measuring pressure in the proximal portion;
   b) disposing a pressure sensor in contact with the distal portion and measuring pressure in the distal portion;
   c) determining strain on the tubing segment from the pressure sensors and generating signals indicative of strain on the tubing segment; and
   d) modifying the number of rotations of the rotor during the running period responsive to signals from the pressure sensors.

2. The method of claim 1, wherein step (c) comprises, more specifically, determining strain on the proximal portion of the tubing segment during the stopped period to obtain a strain stopped.

3. The method of claim 2, wherein step (c) further comprises determining strain on the proximal portion of the tubing segment during the running period to obtain a strain running.

4. The method of claim 3, wherein step (d) comprises, more specifically, subtracting the strain running from the strain stopped to achieve a delta strain and modifying the number of rotations of the rotor during the running period responsive to a magnitude of the delta strain.

5. The method of claim 4, wherein the number of rotations of the rotor during the running period is modified proportionally to the delta strain.

6. The method of claim 3, wherein step (d) comprises, more specifically, subtracting the strain running from the strain stopped to achieve a delta strain and comparing the delta strain to an empirically determined threshold.

7. The method of claim 6, wherein step (d) further comprises stopping operation of the motor unit if the delta strain exceeds the threshold.

8. The method of claim 6, wherein step (d) further comprises generating a warning signal when the delta strain exceeds the threshold.

9. The method of claim 6, wherein step (d) comprises, more specifically, modifying the number of rotations of the rotor during the running period proportionately to the delta strain if the delta strain is below the threshold.

10. The method of claim 9, wherein step (d) comprises, more specifically, increasing the rate of rotation of the rotor.

11. The method of claim 9, wherein step (d) comprises, more specifically, maintaining the rate of rotation of the rotor and increasing the running period's duration.

12. The method of claim 1, wherein step (c) comprises monitoring the pressure in the distal portion of the tubing segment to obtain a reading indicating actual back pressure strain.

13. The method of claim 12 wherein step (d) comprises, more specifically, modifying the number of rotations of the rotor during the running period responsive to the back pressure strain reading.

14. The method of claim 13 wherein step (d) further comprises subtracting an empirically determined back pressure reading from the actual back pressure strain to obtain an excess strain reading prior to modification of the number of rotations of the rotor during the running period.

15. The method of claim 14, wherein the excess strain reading is multiplied by an empirically derived constant to determine an actual fluid output of the pump.

16. The method of claim 15, wherein the number of rotations of the rotor during the running period is increased until the actual fluid output of the pump equals the desired output.

17. The method of claim 16, wherein the running period is lengthened so that the rotor rotates an increased number of times during the running period while maintaining a consistent rotation rate.

18. The method of claim 12, wherein step (d) comprises, more specifically, comparing the actual back pressure reading to an empirically derived threshold.

19. The method of claim 18, wherein step (d) further comprises stopping rotation of the rotor if the actual back pressure exceeds the threshold.

20. The method of claim 18, wherein step (d) further comprises emitting a warning signal when the actual back pressure exceeds the threshold.

21. A method for obtaining a desired output from an enteral feeding pump having a motor unit attached to a rotor to rotate the rotor a number of rotations during a running period and to not rotate the rotor during a stopped period, and a tubing segment extending around the rotor so as to have a proximal portion and a distal portion, the method comprising:

a) disposing a pressure sensor in contact with the proximal portion;

b) monitoring strain on the proximal portion tubing segment during the stopped period and generating signals indicative of strain on the tubing segment during the stopped period; and c) monitoring strain on the proximal portion of the tubing segment during the running period and generating signals indicative of strain on the tubing segment during the running period;

d) comparing the signals indicative of strain on the proximal portion of the tubing segment during the stopped period to the signals indicative of strain on the proximal portion of the tubing segment during the running period to develop a signal indicating the difference between the strain during the stopped period and the strain during the running period; and e) modifying the number of rotations of the rotor responsive to the magnitude of difference between the strain during the stopped period and the strain during the running period.

22. The method of claim 21, wherein step (e) further comprises comparing the difference between strain during the stopped period and strain during the running period to a threshold, and stopping rotation of the rotor if the difference is greater than the threshold.

23. The method of claim 22, further comprising emitting a warning signal when the difference between strain during the running period and strain during the stopped period exceeds the threshold.

24. The method of claim 21, wherein step (e) comprises, more specifically, causing the number of rotations of the rotor during the running period to increase responsive to the magnitude of the difference between strain during the running period and strain during the stopped period.

25. The method of claim 21, wherein the method comprises repeating steps (b) through (e) until an actual output of the enteral feeding pump matches the desired output of the enteral feeding pump.

26. A method for obtaining a desired output from an enteral feeding pump having a motor unit attached to a rotor to rotate the rotor a number of rotations during a running period and to not rotate the rotor during a stopped period, and a tubing segment extending around the rotor so as to have a proximal portion and a distal portion, the method comprising:

a) disposing a pressure sensor in contact with the distal portion;

b) monitoring strain on the distal portion tubing segment during the running period and generating signals indicative of strain on the distal portion of the tubing segment caused by back pressure during the running period; and c) comparing the generated signals to a predetermined threshold; and d) stopping the rotor if the signals indicative of strain on the distal portion of the tubing segment exceed the predetermined threshold.

27. The method of claim 26, wherein the method further comprises, comparing the generated signals indicative of strain on the distal portion of the tubing segment to a predetermined nominal strain value and increasing the number of rotations of the rotor if the signals generated are higher than the nominal strain value and lower than the threshold.

28. The method of claim 27, wherein the method further comprises subtracting the nominal strain value from the signals generated to achieve a value for strain above nominal strain, and multiplying the value for strain above nominal strain by an empirically determined value to determine actual infusion infused.

29. The method of claim 28, wherein the method further comprises increasing the number of rotations of the rotor to increase the volume infused from the actual volume infused to a desired output.

* * * * *